United States Patent
Baumgart

(10) Patent No.: US 9,320,486 B2
(45) Date of Patent: Apr. 26, 2016

(54) SYSTEM FOR VIEWING VASCULATURE AND PERFUSE TISSUE

(71) Applicant: John Baumgart, Hoffman Estates, IL (US)

(72) Inventor: John Baumgart, Hoffman Estates, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 91 days.

(21) Appl. No.: 14/064,470

(22) Filed: Oct. 28, 2013

(65) Prior Publication Data
US 2014/0133731 A1     May 15, 2014

Related U.S. Application Data

(60) Provisional application No. 61/726,035, filed on Nov. 14, 2012.

(51) Int. Cl.
    *G06K 9/00*     (2006.01)
    *A61B 6/00*     (2006.01)
    *G06T 5/50*     (2006.01)

(52) U.S. Cl.
    CPC .............. *A61B 6/504* (2013.01); *A61B 6/481* (2013.01); *A61B 6/486* (2013.01); *A61B 6/5229* (2013.01); *G06T 5/50* (2013.01); *A61B 6/4441* (2013.01); *G06T 2207/10116* (2013.01); *G06T 2207/20221* (2013.01); *G06T 2207/20224* (2013.01)

(58) Field of Classification Search
None
See application file for complete search history.

(56) References Cited

U.S. PATENT DOCUMENTS

| | | | | | |
|---|---|---|---|---|---|
| 4,444,196 | A | * | 4/1984 | Stein | G06T 5/50 348/E5.086 |
| 4,504,908 | A | * | 3/1985 | Riederer | A61B 6/481 128/922 |
| 4,551,800 | A | * | 11/1985 | Riederer | G06T 5/50 128/922 |
| 6,134,353 | A | * | 10/2000 | Makram-Ebeid | G06T 7/0083 382/128 |
| 7,822,242 | B2 | | 10/2010 | Kobayashi et al. | |
| 8,150,127 | B2 | | 4/2012 | Baumgart | |
| 8,299,413 | B2 | * | 10/2012 | Vogt | G06T 5/50 250/208.1 |
| 8,355,557 | B2 | * | 1/2013 | Chen | G06T 5/50 378/4 |
| 8,437,519 | B2 | | 5/2013 | Baumgart et al. | |
| 8,463,012 | B2 | | 6/2013 | Rauch et al. | |
| 8,848,996 | B2 | * | 9/2014 | Baumgart | A61B 5/14 128/922 |
| 2008/0027316 | A1 | * | 1/2008 | Baumgart | A61B 6/463 600/425 |
| 2008/0101670 | A1 | * | 5/2008 | Baumgart | G06T 5/50 382/128 |
| 2009/0016483 | A1 | * | 1/2009 | Kawasaki | A61B 5/02007 378/4 |
| 2009/0257631 | A1 | * | 10/2009 | Baumgart | G06T 5/50 382/128 |

(Continued)

OTHER PUBLICATIONS

English translation of Office Action in counterpart Chinese application No. 201310757218.7 dated Aug. 18, 2015, 17 pages.

*Primary Examiner* — Chan Park
*Assistant Examiner* — Iman K Kholdebarin

(57) ABSTRACT

A system and method includes reception of a mask x-ray image of a patient volume, reception of a plurality of sequential x-ray images of the patient volume including a contrast medium, subtraction of the mask x-ray image from each of the plurality of sequential x-ray images to generate a plurality of sequential x-ray difference images, filtering of each of the plurality of sequential x-ray difference images based on one or more filter parameters to generate a plurality of sequential filtered x-ray difference images, combination of each of the plurality of sequential filtered x-ray difference images with a corresponding one of the plurality of sequential x-ray difference images based on a weight to generate a plurality of combined sequential x-ray images, and display of the plurality of combined sequential x-ray images sequentially.

24 Claims, 14 Drawing Sheets

(56) References Cited

U.S. PATENT DOCUMENTS

| | | | |
|---|---|---|---|
| 2010/0172474 A1* | 7/2010 | Vogt | G06T 5/50 378/98.12 |
| 2010/0259550 A1 | 10/2010 | Baumgart | |
| 2011/0305378 A1* | 12/2011 | Florent | A61B 6/481 382/130 |
| 2012/0201439 A1* | 8/2012 | Rauch | G06T 7/20 382/130 |
| 2012/0238871 A1* | 9/2012 | Pfister | A61B 6/12 600/431 |
| 2012/0250974 A1* | 10/2012 | Miyamoto | A61B 6/481 382/132 |
| 2013/0216119 A1* | 8/2013 | Baumgart | A61B 5/14 382/134 |
| 2013/0241552 A1* | 9/2013 | Hirai | G01R 33/5607 324/309 |

\* cited by examiner

SYSTEM FOR VIEWING VASCULATURE AND PERFUSE TISSUE

CROSS REFERENCE TO RELATED APPLICATIONS

This application is related to, and claims benefit to and priority of, U.S. Patent Application Ser. No. 61/726,035, filed on Nov. 14, 2012, the contents of which are hereby incorporated by reference in their entirety for all purposes.

BACKGROUND

1. Field

The embodiments described below relate to the processing of angiographic x-ray images acquired while contrast medium is present within a patient volume.

2. Description

According to conventional angiographic x-ray imaging, contrast media are used to enhance the contrast of blood-carrying structures within patient anatomy. For example, contrast medium is introduced into a patient volume (e.g., via intravenous injection) and an x-ray image of the volume is acquired while the medium is located within the volume. In the x-ray image, structures which contain the medium appear darker than they would otherwise appear.

According to DSA (Digital Subtraction Angiography), a "mask image" of the patient volume is subtracted from an x-ray image acquired as described above. The mask image is acquired without the presence of the contrast medium and represents background anatomic detail. The resulting image is intended to portray only the vessel and perfuse tissue components of the patient volume which include contrast medium.

Systems are desired which provide efficient presentation of different blood-carrying components of the patient volume.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

Some embodiments provide display of large vasculature excluding perfusion in the capillaries, or capillary perfusion excluding vasculature, and/or a selective blend thereof that is not provided by current x-ray imaging systems.

The following description is provided to enable any person in the art to make and use the described embodiments and sets forth the best mode contemplated for carrying out the described embodiments. Various modifications, however, will remain readily apparent to those in the art.

Figure 1:
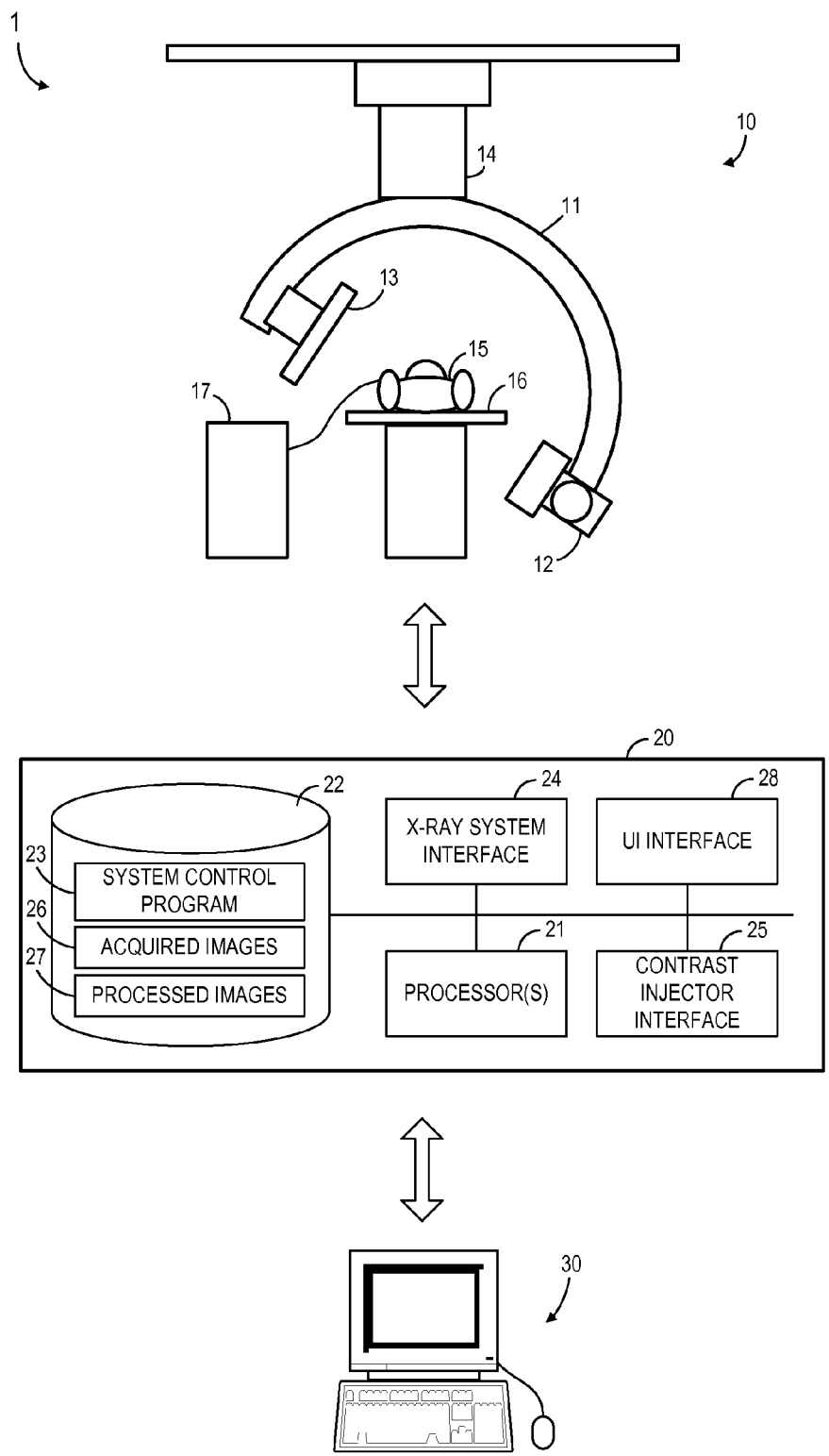
FIG. 1 illustrates a system according to some embodiments.

FIG. 1 illustrates system 1 according to some embodiments. System 1 includes x-ray imaging system 10, control and processing system 20, and operator terminal 30. Generally, and according to some embodiments, x-ray imaging system 10 introduces contrast medium into a patient volume and acquires x-ray images of the patient volume. Control and processing system 20 controls x-ray imaging system 10 and receives the acquired images therefrom. Control and processing system 20 processes the images as described below and provides the processed images to terminal 30 for display thereby. Such processing may be based on user input received by terminal 30 and provided to control and processing system 20 by terminal 30.

X-ray imaging system 10 comprises C-arm 11 on which radiation source 12 and radiation detector 13 are mounted. C-arm 11 is mounted on support 14 and is configured to translate clockwise or counter-clockwise with respect to support 14. This translation rotates radiation source 12 and radiation detector 13 around a central volume while maintaining the physical relationship therebetween. Embodiments are not limited to C-arm-based imaging systems.

Radiation source 12 may comprise any suitable radiation source, including but not limited to a Diabolo™ x-ray tube. In some embodiments, radiation source 12 emits electron, photon or other type of radiation having energies ranging from 50 to 150 keV.

Radiation detector 13 may comprise any system to acquire an image based on received x-ray radiation. In some embodiments, radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In other embodiments, radiation detector 13 converts received photons to electrical charge without requiring a scintillator layer. The photons are absorbed directly by an array of amorphous selenium photoconductors. The photoconductors convert the photons directly to stored electrical charge. Radiation detector 13 may comprise a CCD or tube-based camera, including a light-proof housing within which are disposed a scintillator, a mirror, and a camera.

The charge developed and stored by radiation detector 13 represents radiation intensities at each location of a radiation field produced by x-rays emitted from radiation source 12. The radiation intensity at a particular location of the radiation field represents the attenuative properties of tissues lying along a divergent line between radiation source 12 and the particular location of the radiation field. The set of radiation intensities acquired by radiation detector 13 may therefore represent a two-dimensional projection image of these tissues.

Contrast injector 17 may comprise any known device or devices suitable to controllably introduce contrast medium into a patient volume. As described above, structures which contain contrast medium appear darker in x-ray images than they would otherwise appear. Contrast injector 17 may include a reservoir for each of one or more contrast media, and a patient interface such as medical-grade tubing terminating in a hollow needle.

System 20 may comprise any general-purpose or dedicated computing system. Accordingly, system 20 includes one or more processors 21 configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. One or more processors 21 may execute system control program 23 to move C-arm 14, to cause radiation source 12 to emit radiation, to control detector 13 to acquire an image, to cause injector 17 to introduce contrast medium into a volume of patient 15, and to perform any other function. In this regard, system 20 includes x-ray system interface 24 and contrast injector interface 25 for communication with system 10.

Images acquired from system 10 are stored in data storage device 22 as acquired images 26, in DICOM or another data format. Each acquired image 26 may be further associated with details of its acquisition, including but not limited to imaging plane position and angle, imaging position, radiation source-to-detector distance, patient anatomy imaged, patient position, contrast medium bolus injection profile, x-ray tube voltage, image resolution and radiation dosage.

Processor(s) 21 may execute system control program 23 to process acquired images 26, resulting in processed images 27. Processed images 27 may be provided to terminal 30 via UI interface 28 of system 20. UI interface 28 may also receive input from terminal 30, which is used to control processing of acquired images 26 as described below.

Terminal 30 may simply comprise a display device and an input device coupled to system 20. Terminal 30 displays processed images 27 received from system 20 and receives user input specifying filter parameters and/or weights. The filter parameters and/or weights are transmitted to system 20 and used thereby to generate new processed images 27 for subsequent display by terminal 30. In some embodiments, terminal 30 is a separate computing device such as, but not limited to, a desktop computer, a laptop computer, a tablet computer, and a smartphone.

Each of system 10, system 20 and terminal 30 may include other elements which are necessary for the operation thereof, as well as additional elements for providing functions other than those described herein.

According to the illustrated embodiment, system 20 controls the elements of system 10. System 20 also processes images received from system 10. Moreover, system 20 receives input from terminal 30 and provides processed images to terminal 30. Embodiments are not limited to a single system performing each of these functions. For example, system 10 may be controlled by a dedicated control system, with the acquired images being provided to a separate image processing system over a computer network or via a physical storage medium (e.g., a DVD).

Figure 2:
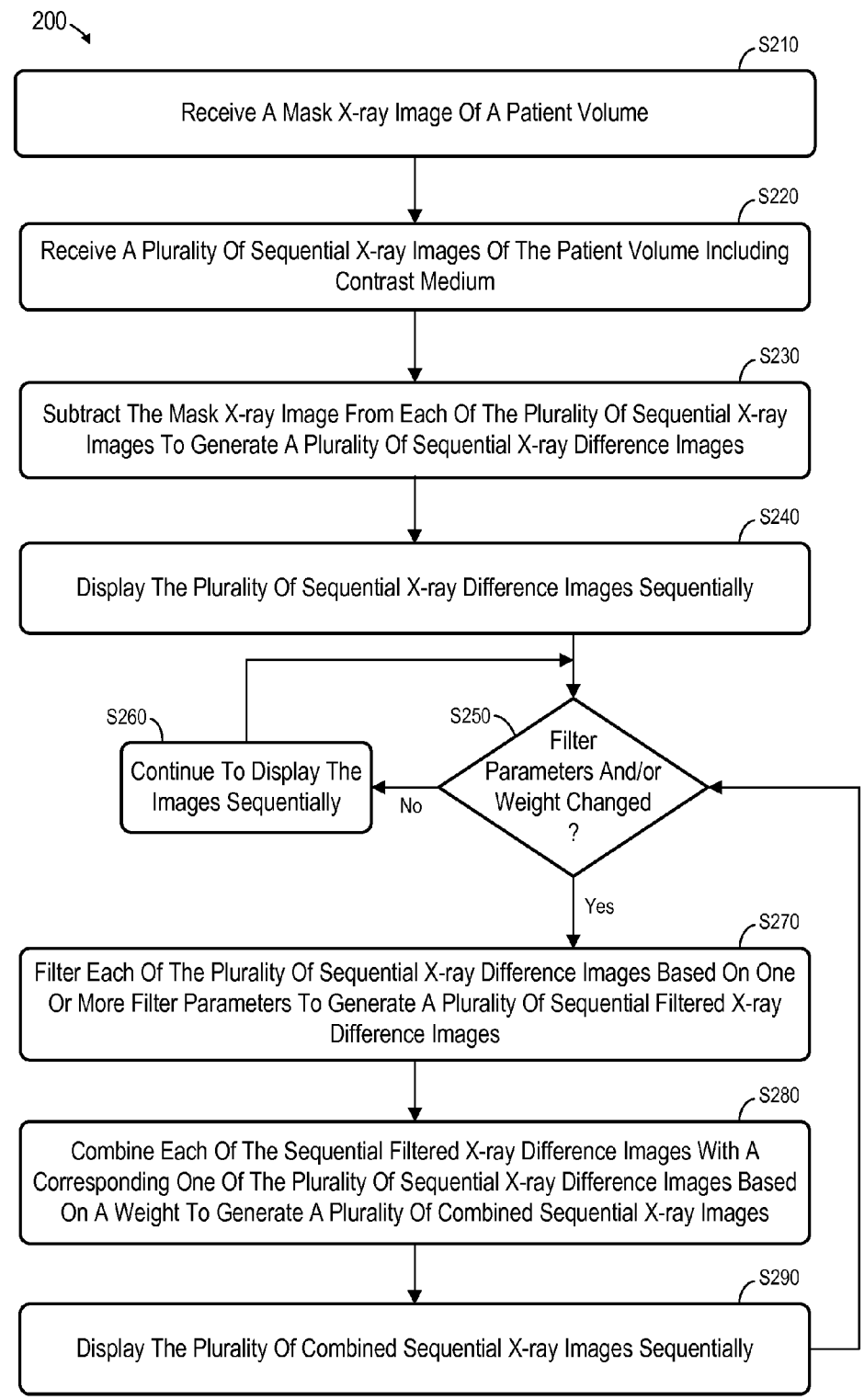
FIG. 2 is a flow diagram of a process according to some embodiments.

In one example of operation according to some FIG. 2 is a flow diagram of process 200 according to some embodiments. Process 200 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape. Examples of these processes will be described below with respect to the elements of system 1, but embodiments are not limited thereto.

Initially, at S210, a mask x-ray image of a patient volume is acquired. As described in the present Background, the mask x-ray image is acquired before introduction of a contrast medium into the patient volume and includes anatomical structure of the patient volume. Next, at S220, a plurality of sequential x-ray images of the patient volume are received, in which the patient volume includes contrast medium.

According to some embodiments, S210 and S220 are performed sequentially while a patient is maintained in a particular imaging position. For example, and with reference to the elements of system 1, patient 15 is positioned on table 16 to place a particular volume of patient 15 between radiation source 12 and radiation detector 13. Table 16 may be adjusted to assist in positioning the patient volume as desired. System 20 then instructs system 10 to move C-arm 11 so that radiation source 12 and radiation detector 13 will generate an image of the patient volume from a desired projection angle.

System 20 also instructs contrast injector 17 to introduce contrast medium into the patient volume. Radiation source 11 is powered by a high-powered generator to emit x-ray radiation toward radiation detector 13 at successive intervals before, during, and after introduction of the contrast medium into the patient volume. The parameters of the medium introduction (e.g., flow rate, location, volume) and x-ray radiation emission (e.g., x-ray tube voltage, dosage) may be controlled by system control program 23 as is known in the art. Radiation detector 13 receives the emitted radiation and produces a set of data (i.e., a projection image) for each interval. The intervals need not be identical in duration.

The mask image of S210 is one of the projection images produced before introduction of the contrast medium into the patient volume, and each of plurality of sequential x-ray images of S220 is a projection image produced while the patient volume includes the contrast medium.

Figure 3:
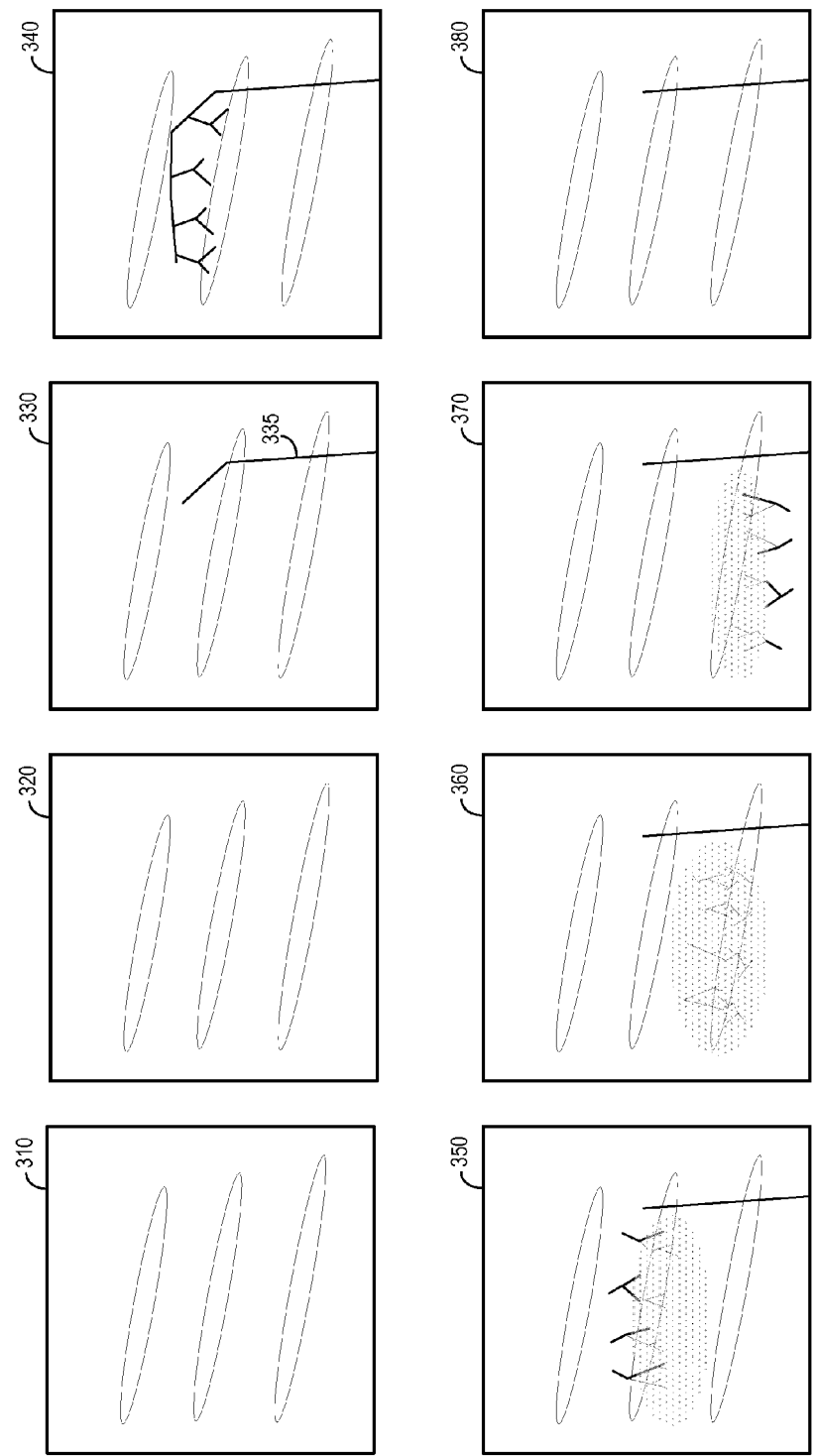
FIG. 3 illustrates x-ray images according to some embodiments.

FIG. 3 includes representations of x-ray images 310-380 received at S210 and S220. Images 310-380 are temporally-successive images in that an image associated with a larger reference numeral was acquired after an image associated with a smaller reference numeral. As mentioned above, x-ray images 310-380 may have been generated by a separate imaging system and received at S210 and S220 by an independent, and possibly remotely-located, image processing system which executes process 200.

According to the FIG. 3 example, x-ray images 310 and 320 were acquired prior to the introduction of contrast medium into the imaged patient volume. X-ray images 310 and 320 therefore include only images of patient anatomy. Images 330 and 340 shows the initial introduction of contrast medium into the arteries within the patient volume, with dark line 385 representing the injection device (e.g., a needle) filled with contrast medium. Image 350 shows the flow of the contrast medium from the arteries into capillary perfusion, image 360 shows capillary perfusion, image 370 shows the flow of the contrast medium from capillary perfusion into veins, and image 380 shows the patient volume after washout of the contrast medium.

Figure 4:
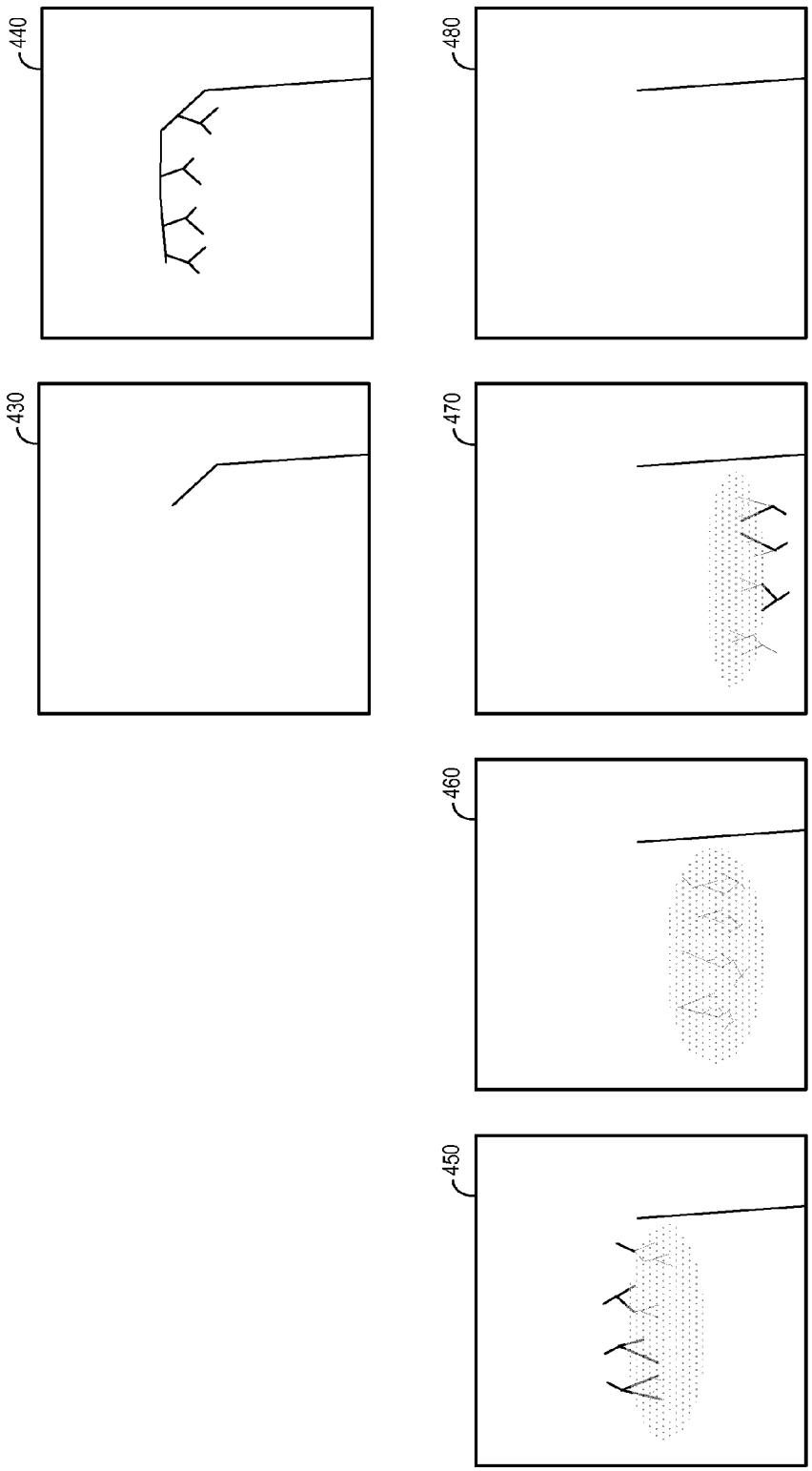
FIG. 4 illustrates difference x-ray images according to some embodiments.

Returning to process 200, the mask image received at S210 is subtracted from each of the plurality of sequential x-ray images at S230. The resulting images are referred to herein as the plurality of sequential x-ray difference images. This subtraction may be performed as is known in the art, for example, by registering image 320 again each of the plurality of sequential x-ray images and subtracting the associated registered image therefrom. FIG. 4 illustrates a plurality of sequential x-ray difference images 430-480 generated at S230 based on mask image 320 and sequential x-ray images 330-380 of FIG. 3.

Figure 5:
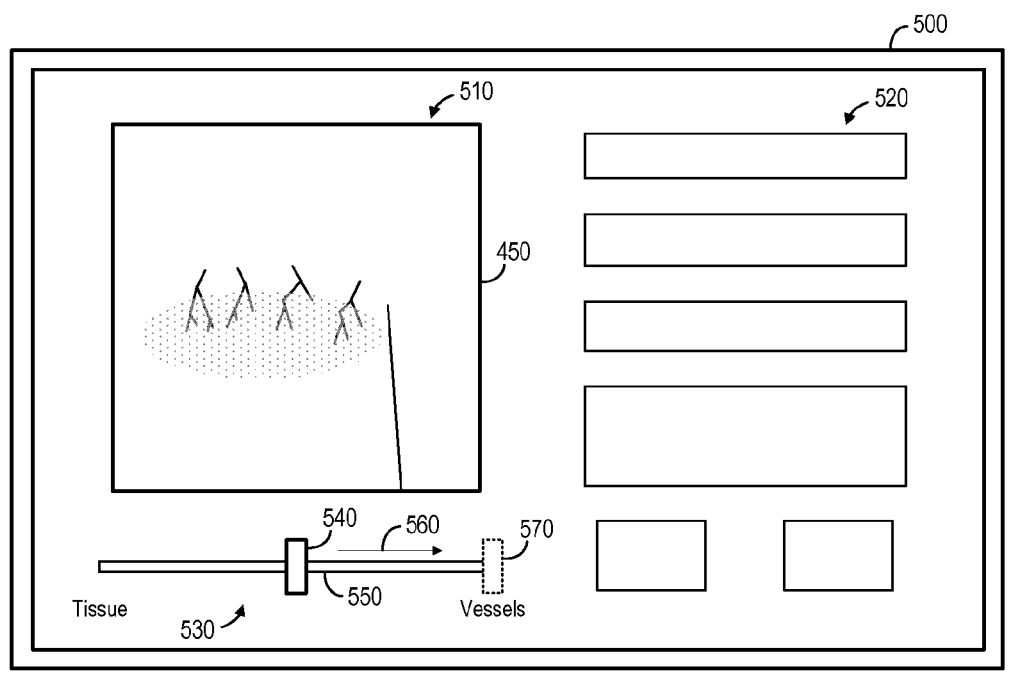
FIG. 5 illustrates a user interface according to some embodiments.

Next, at S240, the plurality of sequential x-ray difference images 430-480 are initially displayed sequentially. FIG. 5 illustrates interface 500 for displaying a plurality of sequential x-ray difference images according to some embodiments. Interface 500 may be displayed by a display device of terminal 30 in response to execution of program code of system control program 23 by processor(s) 21.

Interface 500 includes area 510 for displaying x-ray images. The displayed images may be images acquired by imaging system 10 and/or x-ray images generated based on acquired images according to some embodiments. Area 510 of FIG. 5 shows x-ray image 450 of FIG. 4.

Interface 500 also includes areas 520 for displaying any suitable information that is or becomes known. For example, in a case that interface 500 is displayed to an operator during image acquisition, areas 520 may present one or more image acquisition parameters, patient biometric data, or the like. Areas 520 may also or alternatively display information relating to images displayed in area 510, such as, but not limited to, histograms, filtering parameters, and biological information determined based on the images.

Areas 520 may also or alternatively include one or more user interface controls. These controls may allow an operator to change image acquisition parameters, to change the information displayed by interface 500, to control image processing performed by system 20, or to perform any other suitable operation.

In this regard, an operator operates control 530 in some embodiments to transmit filter parameters and weights to an image processing system such as system 20. Control 530 consists of slider 540 and slider bar 550. An operator may move slider 540 along slider bar 550 using a touchscreen, a mouse, a keyboard or any other input device. As will be described in detail below, the filter parameters and weights associated with each position of slider 540 are used to generate images for display in area 510.

Embodiments are not limited to the content and arrangement discussed above with respect to FIG. 5. Any one or more user interface controls may be used to change the filter parameters and weights discussed herein. Such controls include, but are not limited to, text input boxes, dials, gestures, etc. Moreover, in some embodiments, an operator may transmit filter parameters and weights to an image processing system via an input device (e.g., joystick, mouse, touchpad) without the use of any visually manipulable user interface control. In such embodiments, the only visual feedback of thusly-changed parameters and/or weights may be the resulting changes in the displayed sequence of images.

Returning to S240, it will be assumed that images 430 through 480 are displayed sequentially in area 510. According to some embodiments, known processing may be applied to images 430 through 480 prior to their display in order to enhance edges, adjust brightness, collimate the field of view, and/or to conform the images to the display properties of the display device. The images may be displayed in a continuous loop as flow continues through S250.

At S250, it is determined whether filter parameters and/or a weight have changed. According to the present example, the applicable filter parameters and weight are initially "zero", as represented by the center position of slider 540 on slider bar 550. While slider 540 remains in this position, the sequential display of the images continues as flow cycles between S250 and S260.

For purposes of illustrating some embodiments, it is now assumed that the operator uses an input device to move slider 540 as illustrated by arrow 560 to position 570. System 20 receives an indication of this move and determines that at least one of the filter parameters and weight has been changed. Accordingly, flow proceeds from S250 to S270. In some embodiments, the currently-displayed sequence of images continues to be displayed during execution of S270 and S280, until a new sequence of images is ready to be displayed at S290 as described below. Some embodiments allow pausing of the continuous display, independent of the operation of process 200.

At S270, each of the plurality of sequential x-ray difference images is filtered based on one or more filter parameters. The resulting images will be referred to herein as a plurality of sequential filtered x-ray difference images, in order to distinguish these images from the other images discussed herein.

In some embodiments, all positions to the right of the center position are associated with a particular band-pass filter and all positions to the left of the center position are associated with a particular band-reject filter. The particular band-pass filter is intended to pass image data associated with blood vessels. In some embodiments, such a band-pass filter preserves structures of the image data which are between 3 and 40 pixels in size. Conversely, the particular band-reject filter associated with positions to the left of the center position is intended to suppress structures of the image data which are between 3 and 40 pixels in size, in order to preserve and accentuate perfuse tissue.

Figure 6:
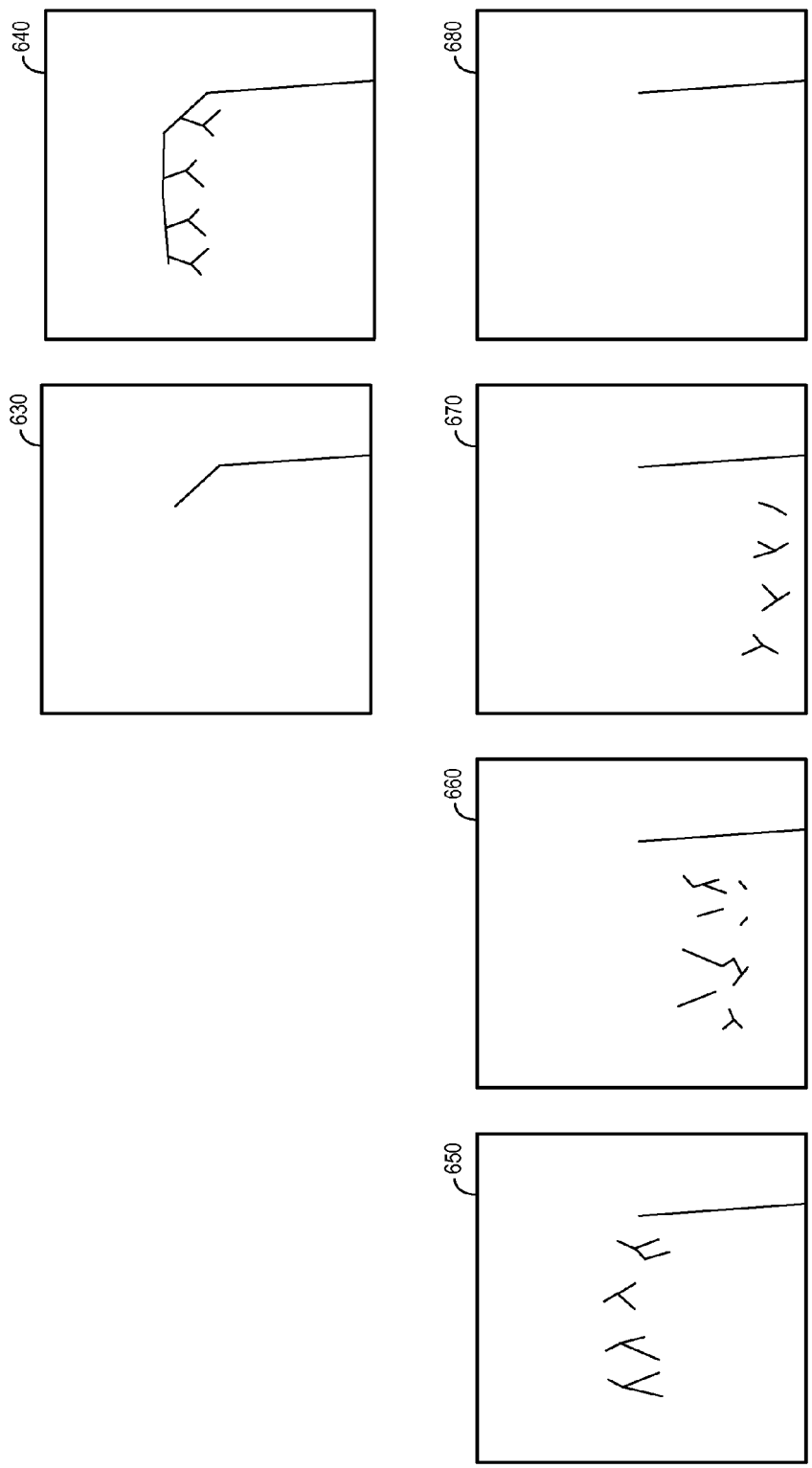
FIG. 6 illustrates filtered x-ray images according to some embodiments.

Therefore, in response to the movement of slider 540 to position 570, each of the plurality of sequential x-ray difference images is filtered based on a band-pass filter. FIG. 6 shows sequential filtered x-ray difference images 630-680 which are generated based on images 430-480 and a band-pass filter according to the present example. As shown, small structures of images 430-480 have been filtered out of images 630-680.

At S280, each of the images generated at S270 is combined with a corresponding one of the images generated at S230 based on a weight. According to some embodiments, the weight indicates an amount to which each image contributes to the resulting combined image. For example, a weight of 0.75 might indicate that image 630 will be weighted three times more heavily than corresponding image 430 (i.e., 0.75 vs 0.25) when combining image 630 with image 430 to generate a corresponding combined image at S280. Any suitable weight-based combination algorithm may be utilized at S280.

In the present example, position 570 indicates a weight of 1. Therefore, images 630-680 are weighted 100% and images 430-480 are weighted 0% when generating the resulting combined images at S280. That is, the combined images are identical to images 630-680. The combined images are displayed sequentially at S290 and flow returns to S250 to await a next change to the filter parameters and/or weight.

Known processing may be applied to the combined images after S280 and prior to their display at S290. As mentioned above, such processing may enhance edges, adjust brightness, collimate the field of view, and/or to conform the images to the display properties of the display device.

Figure 7:
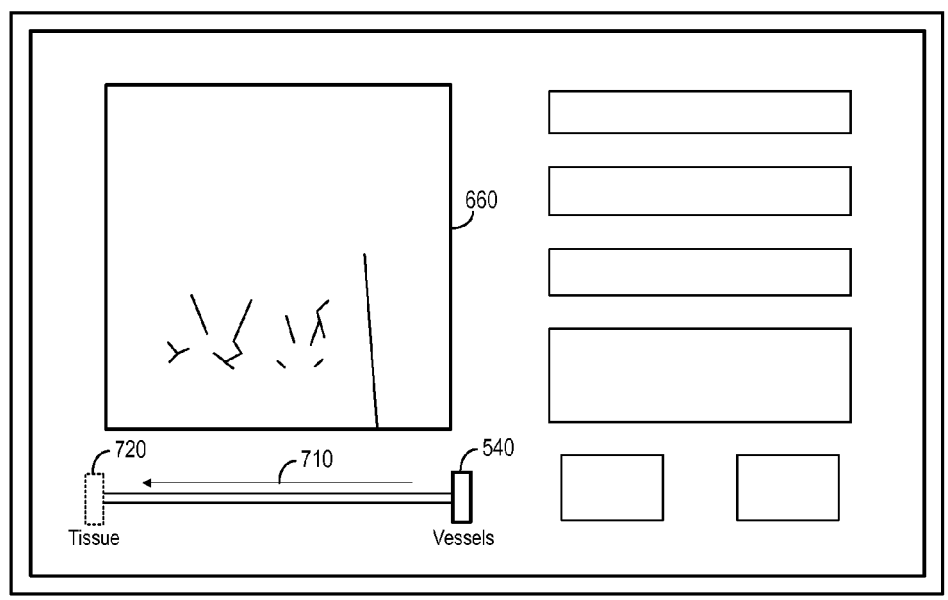
FIG. 7 illustrates a user interface according to some embodiments.

FIG. 7 illustrates display of one of the combined images as flow cycles between S250 and S260 according to the present example. As mentioned above, the sequentially and continuously-displayed combined images are identical to images 630-680, therefore FIG. 7 illustrates the display of image 660.

It will now be assumed that the operator moves slider 540 in the direction of arrow 710 to position 720. Flow therefore proceeds from S250 to S270. Position 720 of the present example corresponds to a band-reject filter and a weight of 1. Therefore, at S270, each of the plurality of sequential x-ray difference images generated at S230 is filtered based on the band-reject filter to generate a new plurality of sequential filtered x-ray difference images.

Figure 8:
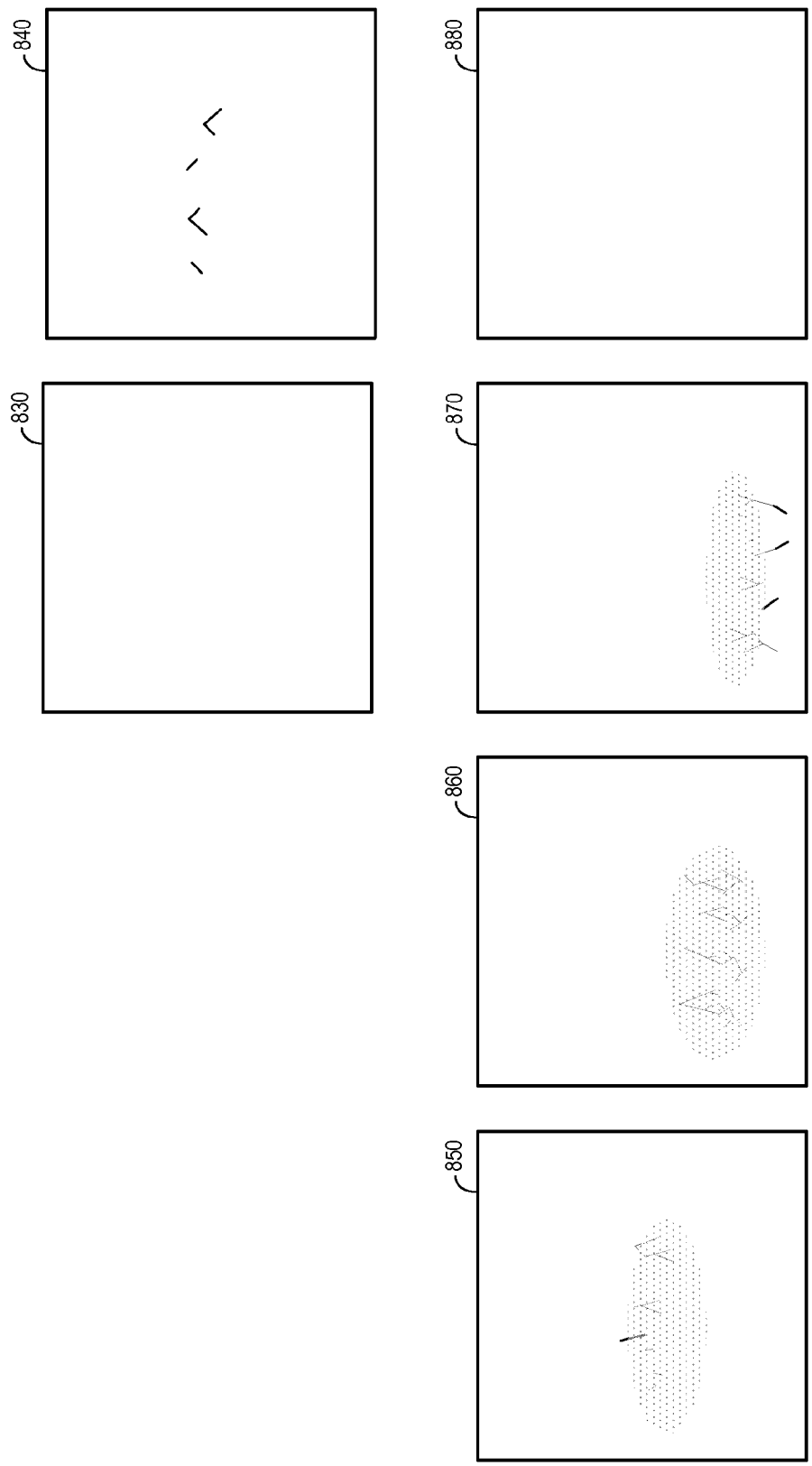
FIG. 8 illustrates filtered x-ray images according to some embodiments.

FIG. 8 shows sequential filtered x-ray difference images 830-880 which are generated based on images 430-480 and a band-reject filter according to the present example. As shown, larger structures of images 430-480 have been filtered out of images 830-880.

Since position 720 indicates a weight of 1, images 830-880 are weighted 100% and images 430-480 are weighted 0% and the combined images generated at S280 are identical to images 830-880. These combined images are displayed sequentially at S290 and flow returns to S250 to await a next change to the filter parameters and/or weight.

Figure 9:
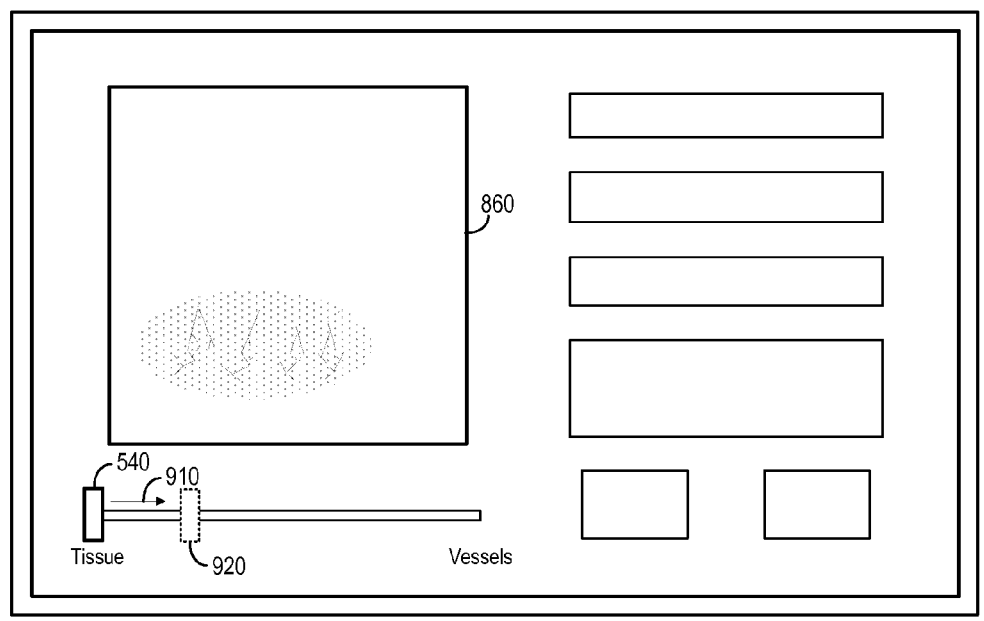
FIG. 9 illustrates a user interface according to some embodiments.

FIG. 9 illustrates the display of image 860 of the combined images as flow returns to S250 and cycles between S250 and S260 according to the present example. As shown, the operator now moves slider 540 in the direction of arrow 910 to position 920.

Since position 920 is on the left side of bar 550, each of the plurality of sequential x-ray difference images generated at S230 is filtered at S270 based on the band-reject filter to generate a plurality of sequential filtered x-ray difference images. According to the present example, the band-reject filter is the same as previously-discussed, so the images generated at S270 are images 830-880 of FIG. 8. According to some embodiments, filtered images 830-880 and 630-680 may be cached after their initial generation in order to eliminate the need to re-generate these images.

Flow then proceeds to S280. Unlike the examples described above, position 920 corresponds to a weight between 0 and 1. Therefore, each combined image generated at S280 will include portions of its corresponding filtered and unfiltered images. For example, it is assumed that position 920 corresponds to a weight of 0.5. Accordingly, at S280, the filtered images generated at S270 and the difference images of S230 will be equally combined to generate a plurality of combined sequential x-ray images.

Figure 10:
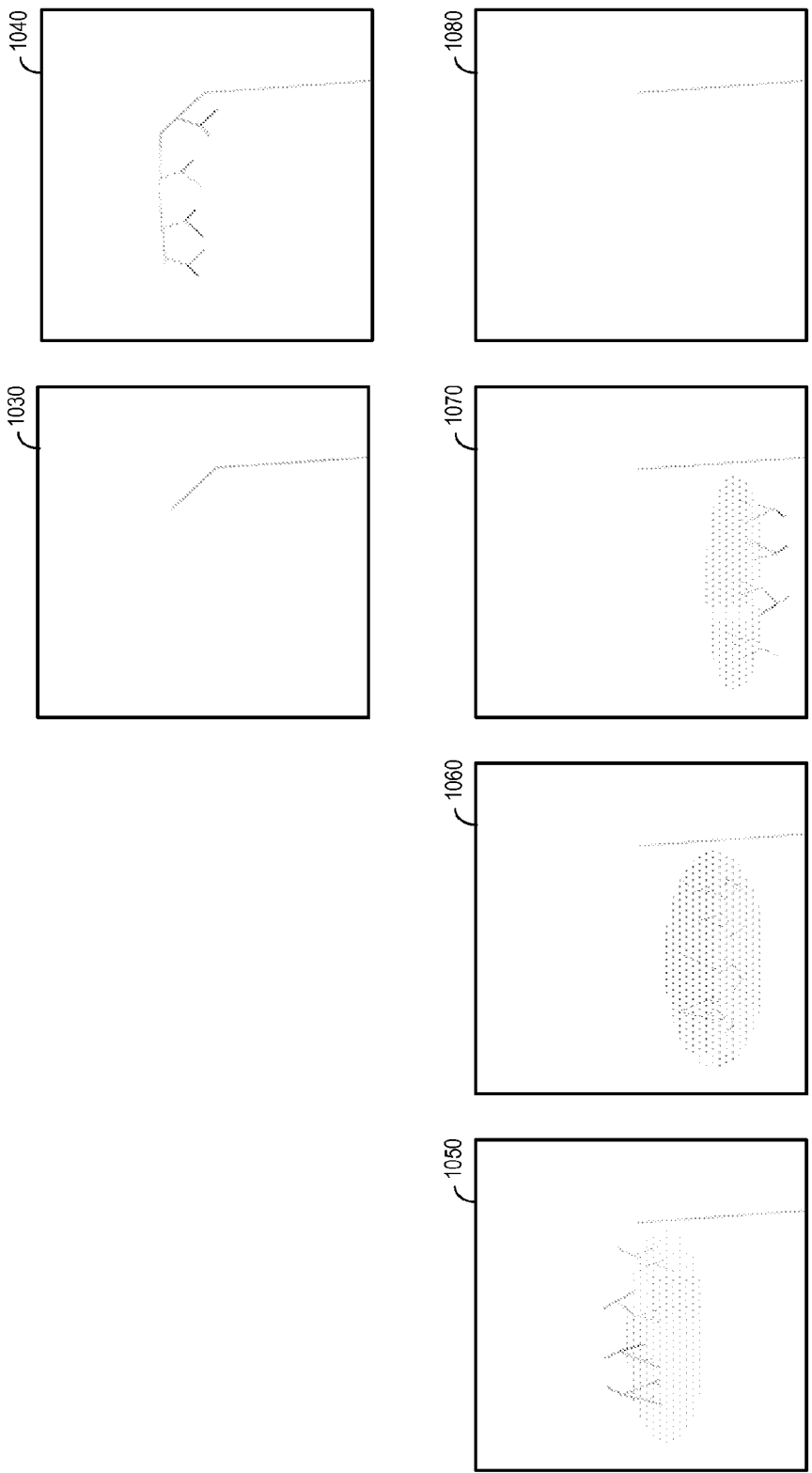
FIG. 10 illustrates combined x-ray images according to some embodiments.
Figure 11:
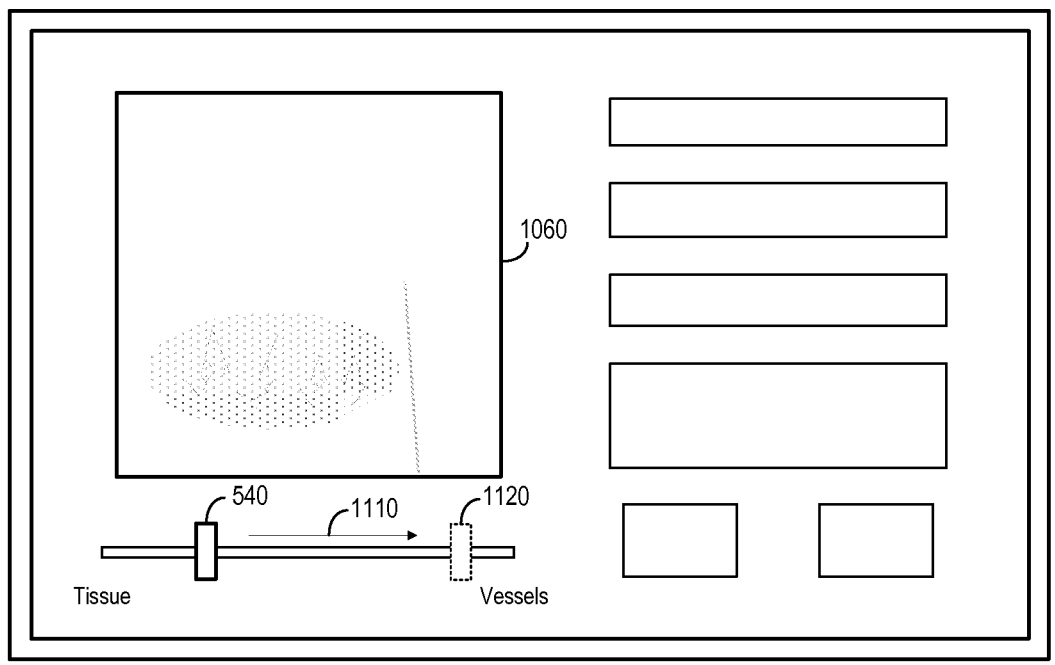
FIG. 11 illustrates a user interface according to some embodiments.

FIG. 10 shows combined sequential filtered x-ray images 1030-1080 which are generated at S280 based on images 430-480 and of images 830-880, and FIG. 11 illustrates display of the combined images at S290 and as flow returns to S250 and cycles between S250 and S260.

FIG. 11 depicts movement of slider 540 in the direction of arrow 1110 to position 1120. Position 1120 is on the right side of bar 550, so each of the plurality of sequential x-ray difference images generated at S230 (e.g., images 430-480) is filtered at S270 based on the above-mentioned band-pass filter to generate a plurality of sequential filtered x-ray difference images. Alternatively, these already-generated filtered x-ray difference images (i.e., images 630-680) are retrieved from a cache.

Next, at S280, the weight corresponding to position 1120 (e.g., 0.75) is used to combine the filtered images generated at S270 with corresponding ones of the difference images of S230. In the present example, the filtered images will be assigned three times (i.e., 0.75×0.25) the weight of the difference images during the combination.

Figure 12:
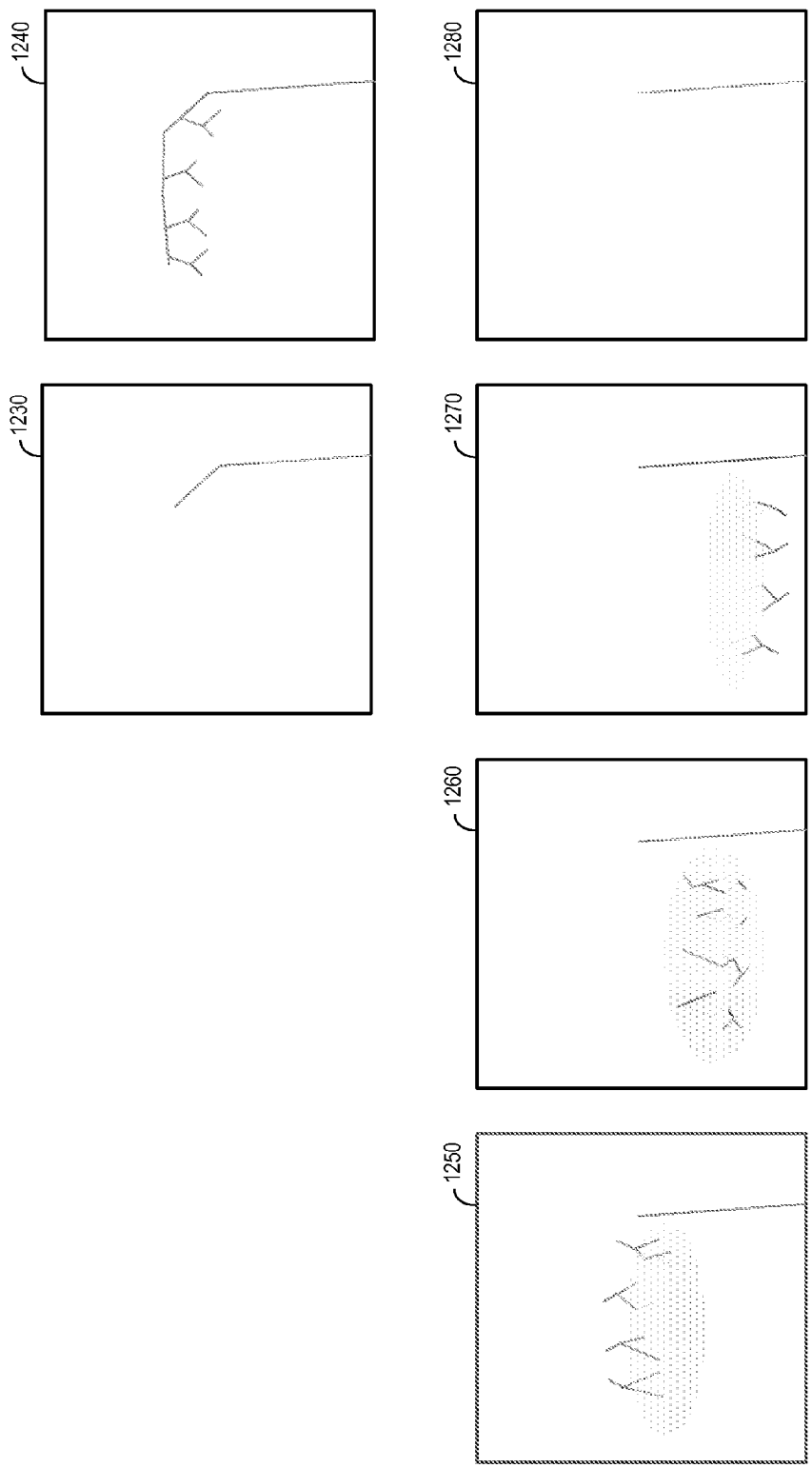
FIG. 12 illustrates combined x-ray images according to some embodiments.
Figure 13:
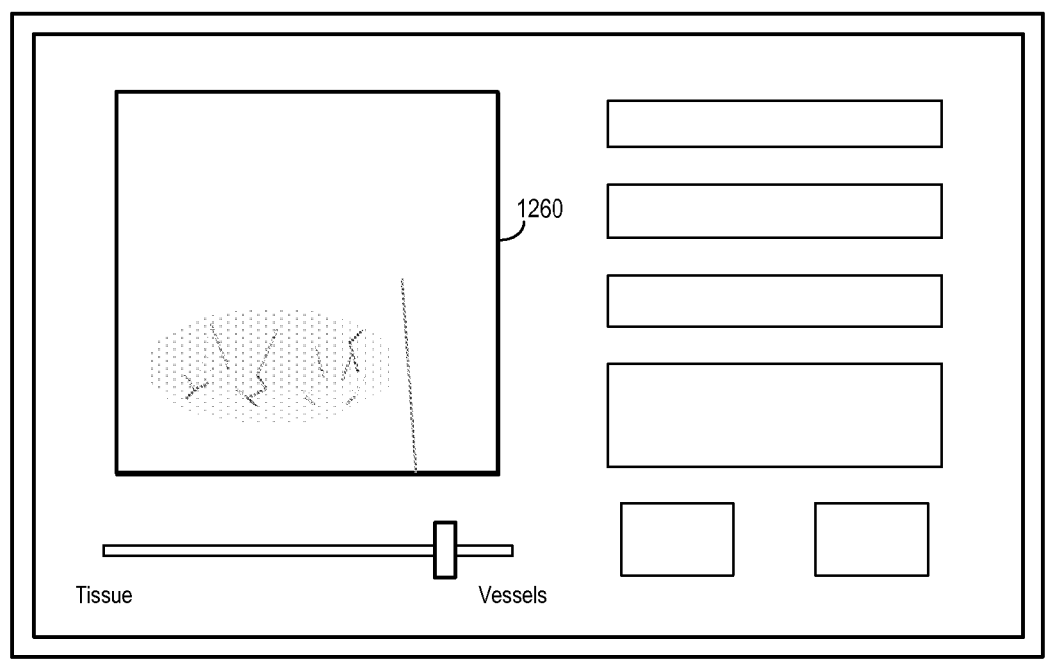
FIG. 13 illustrates a user interface according to some embodiments.

FIG. 12 shows combined sequential filtered x-ray images 1230-1280 which are generated at S280 based on images 430-480 and images 630-680 according to some embodiments. These combined images are displayed sequentially at S290. FIG. 13 illustrates this display, which continues, in a continuous loop, as flow returns to S250 and cycles between S250 and S260.

Some embodiments may therefore efficiently provide gradually-changing depictions of large vasculature excluding perfusion in the capillaries, capillary perfusion excluding vasculature, and/or selective blends thereof that are not provided by current x-ray imaging systems.

Embodiments are not limited to a band-pass filter and a band-reject filter. Moreover, although the present example associates a same band-pass filter with all of the right-of-center positions of slider 540 and a same band-reject filter with all of the left-of-center positions, some embodiments also allow an operator to modify the band which is passed/rejected by filters. Such modifications may occur without modification of the weight used at S280. That is, an operator may simply adjust the size and/or location of the passed/rejected band (without changing the weight) using a suitable user interface control, thereby causing the generation and display of new combined sequential x-ray images as described above.

Figure 14:
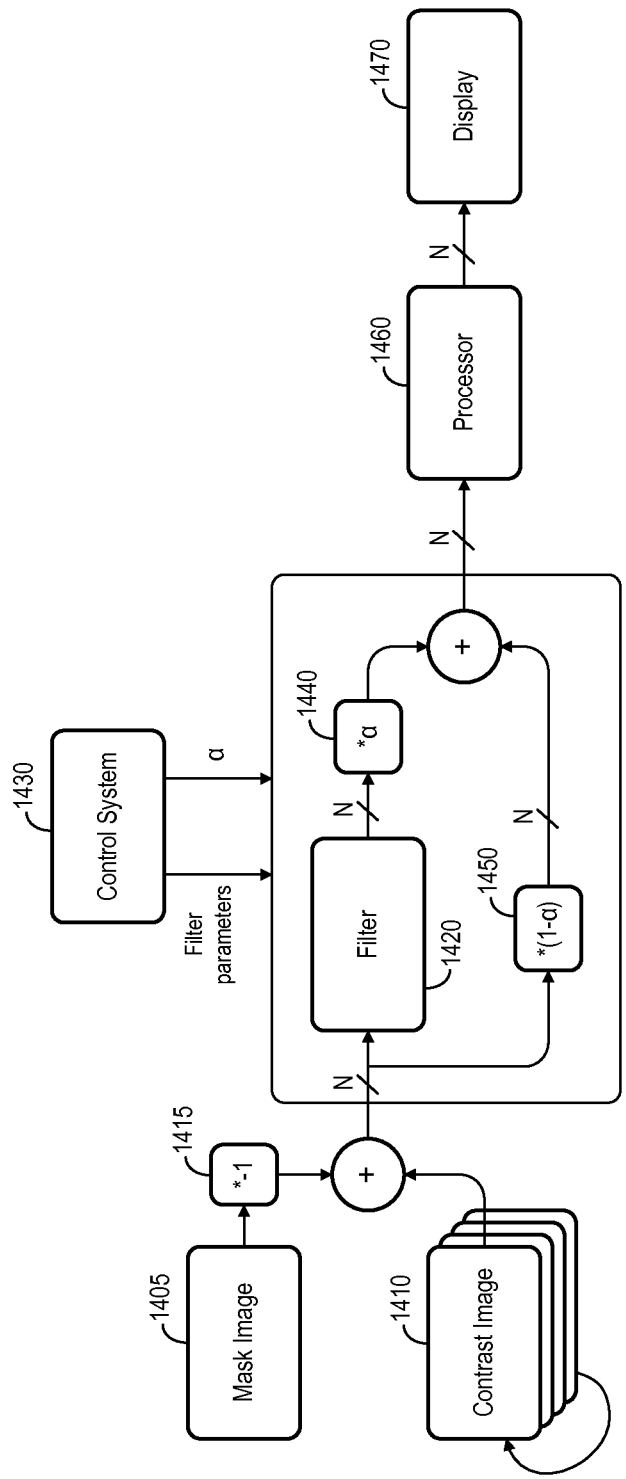
FIG. 14 is a functional block diagram of a system according to some embodiments.

FIG. 14 is a functional block diagram of system 1400 according to some embodiments. Hardware and/or software implementations of system 1400 may execute process 200 according to some embodiments.

For example, mask image 1405 is received at S210 and N sequential "contrast" images 1410 are received at S220. Mask image 1405 is subtracted (element 1415) from each of contrast images 1410 at S230 and filter 1420 is applied to each resulting difference image at S270. Filter 1420 receives filter parameters (e.g., band-pass or band-reject) from control system 1430. Control system 1430 also provides weight a, based on which the filtered images (element 1440) and the difference images (element 1450) are combined at S280. The combined images are subject to additional processing by processor 1460 and then displayed at S290 by display 1470.

Some embodiments operate on color x-ray images. In this regard, a single color x-ray image is received at S220, in which the contrast medium is color-coded to indicate where its presence peaked at different points in time. Process 200 operates as described above to generate a single image at S280, which is a weighted combination of the mask-subtracted original color image and a band-pass/band-reject-filtered version of the mask-subtracted original color image.

Those in the art will appreciate that various adaptations and modifications of the above-described embodiments can be configured without departing from the scope and spirit of the claims. Therefore, it is to be understood that the claims may be practiced other than as specifically described herein.

What is claimed is:
1. A system comprising:
an interface to:
receive a mask x-ray image of a patient volume; and
receive a plurality of sequential x-ray images of the patient volume including a contrast medium;
an image data processor to:
subtract the mask x-ray image from each of the plurality of sequential x-ray images to generate a plurality of sequential x-ray difference images;

filter each of the plurality of sequential x-ray difference images based on one or more filter parameters to generate a plurality of sequential filtered x-ray difference images;

combine each of the plurality of sequential filtered x-ray difference images with a corresponding one of the plurality of sequential x-ray difference images based on a weight to generate a plurality of combined sequential x-ray images;

filter each of the plurality of sequential x-ray difference images based on a second one or more filter parameters to generate a second plurality of sequential filtered x-ray difference images change filter parameters; and combine each of the second plurality of sequential filtered x-ray difference images with a corresponding one of the plurality of sequential x-ray difference images based on the weight to generate a second plurality of combined sequential x-ray images; and a display to display the plurality of combined sequential x-ray images sequentially, and the second plurality of combined sequential x-ray images sequentially.

2. A system according to claim 1, wherein the image data processor filters each of the plurality of sequential x-ray difference images based on the second one or more filter parameters, and combines each of the second plurality of sequential filtered x-ray difference images with a corresponding one of the plurality of sequential x-ray difference images based on the weight during display of the plurality of combined sequential x-ray images.

3. A system according to claim 2, wherein the one or more filter parameters define a band-reject filter, and the second one or more filter parameters define a band-pass filter.

4. A system according to claim 2, wherein the one or more filter parameters define a first band-reject filter, and the second one or more filter parameters define a second band-reject filter different from the first band-reject filter.

5. A system according to claim 2, wherein the one or more filter parameters define a first band-pass filter, and the second one or more filter parameters define a second band-pass filter different from the first band-pass filter.

6. A system according to claim 1, wherein the one or more filter parameters define a band-reject filter, and the second one or more filter parameters define a band-pass filter.

7. A system according to claim 1, the image data processor further to:

combine each of the second plurality of sequential filtered x-ray difference images with a corresponding one of the plurality of sequential x-ray difference images based on a second weight to generate a second plurality of combined sequential x-ray images; and the display to display the second plurality of combined sequential x-ray images sequentially.

8. A system according to claim 7, wherein the image data processor combines each of the second plurality of sequential filtered x-ray difference images with a corresponding one of the plurality of sequential x-ray difference images based on the second weight during display of the plurality of combined sequential x-ray images.

9. A system according to claim 1, the image data processor further to:

filter each of the plurality of sequential x-ray difference images based on the second one or more filter parameters to generate a second plurality of sequential filtered x-ray difference images; and combine each of the second plurality of sequential filtered x-ray difference images with a corresponding one of the plurality of sequential x-ray difference images based on a second weight to generate an additional plurality of combined sequential x-ray images; and the display to display the additional plurality of combined sequential x-ray images sequentially.

10. A system according to claim 9, wherein the image data processor filters each of the plurality of sequential x-ray difference images based on the second one or more filter parameters, and combines each of the second plurality of sequential filtered x-ray difference images with a corresponding one of the plurality of sequential x-ray difference images based on the weight during display of the plurality of combined sequential x-ray images.

11. A system according to claim 9, wherein the one or more filter parameters define a band-reject filter, and the second one or more filter parameters define a band-pass filter.

12. A system according to claim 11, wherein the image data processor filters each of the plurality of sequential x-ray difference images based on the second one or more filter parameters, and combines each of the second plurality of sequential filtered x-ray difference images with a corresponding one of the plurality of sequential x-ray difference images based on the weight during display of the plurality of combined sequential x-ray images.

13. A method comprising:

receiving a mask x-ray image of a patient volume;

receiving a plurality of sequential x-ray images of the patient volume including a contrast medium;

subtracting the mask x-ray image from each of the plurality of sequential x-ray images to generate a plurality of sequential x-ray difference images;

filtering each of the plurality of sequential x-ray difference images based on one or more filter parameters to generate a plurality of sequential filtered x-ray difference images;

combining each of the plurality of sequential filtered x-ray difference images with a corresponding one of the plurality of sequential x-ray difference images based on a weight to generate a plurality of combined sequential x-ray images;

displaying the plurality of combined sequential x-ray images sequentially;

filtering each of the plurality of sequential x-ray difference images based on a second one or more filter parameters to generate a second plurality of sequential filtered x-ray difference images change filter parameters;

combining each of the second plurality of sequential filtered x-ray difference images with a corresponding one of the plurality of sequential x-ray difference images based on the weight to generate a second plurality of combined sequential x-ray images; and displaying the second plurality of combined sequential x-ray images sequentially.

14. A method according to claim 13, wherein each of the plurality of sequential x-ray difference images is filtered based on the second one or more filter parameters, and each of the second plurality of sequential filtered x-ray difference images is combined with a corresponding one of the plurality of sequential x-ray difference images based on the weight during display of the plurality of combined sequential x-ray images.

15. A method according to claim 14, wherein the one or more filter parameters define a band-reject filter, and the second one or more filter parameters define a band-pass filter.

16. A method according to claim 14, wherein the one or more filter parameters define a first band-reject filter, and the second one or more filter parameters define a second band-reject filter different from the first band-reject filter.

17. A method according to claim 14, wherein the one or more filter parameters define a first band-pass filter, and the second one or more filter parameters define a second band-pass filter different from the first band-pass filter.

18. A method according to claim 13, wherein the one or more filter parameters define a band-reject filter, and the second one or more filter parameters define a band-pass filter.

19. A method according to claim 13, further comprising:
combining each of the second plurality of sequential filtered x-ray difference images with a corresponding one of the plurality of sequential x-ray difference images based on a second weight to generate a second plurality of combined sequential x-ray images; and
displaying the second plurality of combined sequential x-ray images sequentially.

20. A method according to claim 19, wherein the second plurality of sequential filtered x-ray difference images are combined with a corresponding one of the plurality of sequential x-ray difference images based on the second weight during display of the plurality of combined sequential x-ray images.

21. A method according to claim 13, further comprising:
filtering each of the plurality of sequential x-ray difference images based on the second one or more filter parameters to generate a second plurality of sequential filtered x-ray difference images;
combining each of the second plurality of sequential filtered x-ray difference images with a corresponding one of the plurality of sequential x-ray difference images based on a second weight to generate an additional plurality of combined sequential x-ray images; and
displaying the additional plurality of combined sequential x-ray images sequentially.

22. A method according to claim 21, wherein each of the plurality of sequential x-ray difference images is filtered based on the second one or more filter parameters, and each of the second plurality of sequential filtered x-ray difference images is combined with a corresponding one of the plurality of sequential x-ray difference images based on the weight during display of the plurality of combined sequential x-ray images.

23. A method according to claim 21, wherein the one or more filter parameters define a band-reject filter, and the second one or more filter parameters define a band-pass filter.

24. A method according to claim 23, wherein each of the plurality of sequential x-ray difference images is filtered based on the second one or more filter parameters, and each of the second plurality of sequential filtered x-ray difference images is combined with a corresponding one of the plurality of sequential x-ray difference images based on the weight during display of the plurality of combined sequential x-ray images.

* * * * *